United States Patent [19]
Taguchi et al.

[11] Patent Number: 5,864,050
[45] Date of Patent: Jan. 26, 1999

[54] CURABLE RESIN COMPOUND, METHOD FOR PRODUCING THE SAME, AND CURED-RESIN MATERIAL

[75] Inventors: Yoshihiro Taguchi; Shiro Kobayashi; Hiroshi Uyama; Atsushi Nakamura, all of Miyagi-ken, Japan

[73] Assignee: Alps Electric Co., Ltd. and Shiro Koayashi, Japan

[21] Appl. No.: 743,997

[22] Filed: Nov. 4, 1996

[30] Foreign Application Priority Data

Nov. 7, 1995 [JP] Japan ..................................... 7-289026
Sep. 6, 1996 [JP] Japan ..................................... 8-237088

[51] Int. Cl.$^6$ ......................... C08F 138/00; C07C 49/84; C07C 49/796
[52] U.S. Cl. ......................... 568/333; 549/554; 526/285; 526/316; 528/125
[58] Field of Search ........................... 528/125; 526/285, 526/316; 568/333

[56] References Cited

U.S. PATENT DOCUMENTS 4,234,712  11/1980  Keller ..................................... 528/125

FOREIGN PATENT DOCUMENTS 00641    8/1988  China .
1953195  6/1996  Germany .

OTHER PUBLICATIONS

Synthesis and Characterization of Soluble, High Molecular Weight Poly (aromatic diacetylenes), Inventors, Kwock, et al., *American Chemical Society*, 1993, pp. 2935–2940.

"Acetylene–terminated ether–ketone oligomers", Inventors, F. Martinez Nunez, et al., *Polymer*, 1992, vol. 33, No. 15, pp. 3286–3291.

Sachdeva "Toughening of AT–Resms" *Journal of Adhesm* vol. 32 pp. 15–28; 1990.

Loughran "Thermal and Thermal Mechanical Properties of Acetylene Terminated Phenylene Systems" *Organic Coatings Plastics* vol. 43 pp. 777–782; 1980.

*Primary Examiner*—David Buttner
*Attorney, Agent, or Firm*—Brinks Hofer Gilson & Lione

[57] ABSTRACT

The present invention provides a curable resin compound which is soluble in organic solvents and easy to use, and a method for producing the same. The curable resin compound comprises a structure and crosslinkable groups which endcap the structure, the structure comprising three or four non-substituted benzene rings each of which is joined with each adjacent benzene ring by an ether or ketone linkage so that both types of linkages are present in the structure. Though the curable resin compound exhibits satisfactory solubilities in organic solvents, a composition comprising the compound can be cured by a crosslinking reaction to be insoluble in the organic solvents while being provided with improved solvent resistance and chemical resistance. Accordingly, the present invention also provides a cured-resin material derived from the aforementioned curable resin compound, the cured-resin material being excellent in solvent resistance, chemical resistance and thermal resistance.

3 Claims, No Drawings

CURABLE RESIN COMPOUND, METHOD FOR PRODUCING THE SAME, AND CURED-RESIN MATERIAL

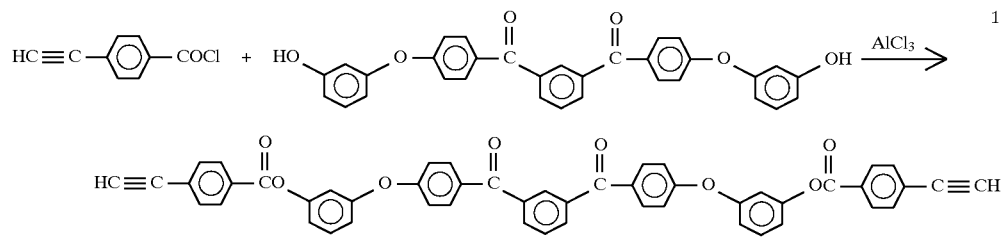

BACKGROUND OF THE INVENTION

1. Field of the Invention

The present invention relates to a synthetic resin compound having excellent thermal and chemical resistance, and excellent mechanical characteristics, wherein the synthetic resin is applicable to a wider variety of molding methods and end-purposes than those of the known art.

2. Description of the Related Art

Poly(ether-ether-ketone)s are known as engineering plastics having excellent thermal and chemical resistances, and excellent mechanical characteristics.

These polymers, however, have a characteristic of high crystallinity, and therefore, they are insoluble in organic solvents.

As a result, only extrusion molding or compression molding can be employed as a molding method for manufacturing various products from these polymers. In other words, the products which can be manufactured by using these polymers are limited.

Accordingly, various research has been performed with the view to make the polymers soluble in organic solvents, and as a result, alkyl-substituted aromatic poly(ether-ketone)s have been developed. Since these alkyl-substituted aromatic poly(ether-ketone)s can be dissolved in various organic solvents, they have been used in many fields; for example, they have been used as common varnish.

These alkyl-substituted aromatic poly(ether-ketone)s soluble in organic solvents are, however, inferior in chemical and solvent resistances, and therefore, cannot be used for products which require these characteristics of the resistance.

J. de. Abajo, et al. reported in POLYMER, Vol.33, No.15, pp.3286–3291 (1992) about a resin compound which was improved in chemical and solvent resistances. This resin compound is produced by the following reaction formula 1.

The above reaction consists of the known Schotten-Baumann reaction, i.e. acylating reaction between 3- or 4-ethynylbenzoylchloride and diol of an aromatic ether-ketone.

The resin compound produced from the above reaction, however, remains insufficiently soluble in the type of organic solvent generally used, and accordingly, molding method options are limited when this resin compound is used.

Further, the resin compound has a structure comprising ester linkages since the Schotten-Baumann reaction is utilized to introduce acetylene groups. As a result, the resin compound is highly moisture-absorptive and tends to be low moistureproof, and in addition, tends to be hydrolyzed by, for example, contact with water vapor. Moreover, since the resin compound is not a polymer, degree of crosslinking cannot be controlled.

Meanwhile, T. M. Miller, et al. reported in Macromolecules, Vol.26, pp.2935–2940 (1993) about a polymer which is produced by the following reaction formula 2.

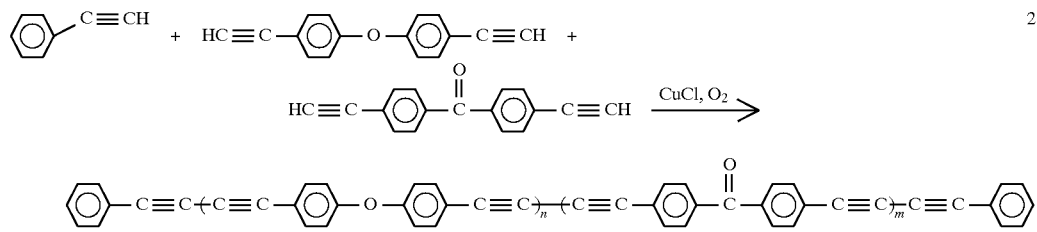

The resultant polymer is produced from an acetylene-terminated aromatic ether monomer and an acetylene-terminated aromatic ketone monomer by using tetramethylethylenediamine, a copper catalyst, or the like.

Such a polymer, however, has some drawbacks. For example, solubility in organic solvents becomes low as the molecular weight of the polymer increases. In addition, control of the polymer molecular weights is not easy. Although the polymer has a ketone group, the polymer has no ether linkages. This causes the principal chain of the polymer to be stiffer, the polymer to be easily dissolved in a solvent, and crosslinking to not easily progress. Moreover, since the curing temperature of the polymer is 300° C. or higher, the polymer rarely can be used in view of the limited thermal capability of furnaces ordinarily used.

SUMMARY OF THE INVENTION

The present invention has been accomplished in order to solve the above-described drawbacks or problems. Accordingly, the object of the present invention is to provide a curable resin compound which is soluble in organic solvents and is easy to use; a cured-resin material based on the curable resin compound, which is excellent in thermal, chemical, and solvent resistances; and a method for producing the curable resin compound.

Specifically, the aspects of the present invention are as follows.

(1) A curable resin compound comprising a structure and crosslinkable groups which end-cap the structure, wherein the structure comprises three or four non-substituted benzene rings each of which is joined with each adjacent benzene ring by an ether linkage or ketone linkage so that both types of linkages are present in the structure.

(2) A curable resin compound comprising a polymer which comprises repeating units and end-capping crosslinkable groups, wherein the repeating unit comprises three or four non-substituted benzene rings each of which is joined with each adjacent benzene ring by an ether linkage or ketone linkage so that both types of linkages are present in the repeating unit and at least one benzene ring in the repeating unit has an ortho- or meta-linkage structure.

(3) The curable resin compound recited in the above paragraph (1) or (2), wherein the crosslinkable groups are thermally crosslinkable groups.

(4) The curable resin compound recited in the above paragraph (1) or (2), wherein the crosslinkable groups are ethynyl groups.

(5) The curable resin compound recited in any one of the above paragraphs (1) to (4), wherein the compound is provided with a treatment for decreasing crystallinity.

(6) A cured-resin material comprising a crosslinked resin compound, wherein the resin compound is the curable resin compound recited in any one of the above paragraphs (1) to (5).

(7) A method for producing a curable resin compound; the curable resin compound comprising a structure and ethynyl groups end-capping the structure, the structure comprising three or four non-substituted benzene rings each of which is joined with each adjacent benzene ring by an ether linkage or ketone linkage so that both types of linkages are present in the structure; wherein the method comprises subjecting an aromatic ether-ketone end-capped with Br, I, or Cl to a reaction with an ethynyl-substituted tertiary alcohol or a silylacetylene in the presence of a palladium catalyst, the aromatic ether-ketone comprising three or four non-substituted benzene rings each of which is joined with each adjacent benzene ring by an ether linkage or ketone linkage so that both types of linkages are present in the ether-ketone.

(8) A method for producing a curable resin compound; the curable resin compound comprising a polymer which comprises repeating units and end-capping ethynyl groups, the repeating unit comprising three or four non-substituted benzene rings each of which is joined with each adjacent benzene ring by an ether linkage or ketone linkage so that both types of linkages are present in the repeating unit and at least one benzene ring in the repeating unit has an ortho- or meta-linkage structure; wherein the method comprises subjecting a polymer end-capped with Br, I, or Cl to a reaction with an ethynyl-substituted tertiary alcohol or a silylacetylene in the presence of a palladium catalyst, the polymer comprising repeating units comprising three or four non-substituted benzene rings each of which is joined with each adjacent benzene ring with an ether linkage or ketone linkage so that both types of linkages are present in the repeating unit and at least one benzene ring in the repeating unit has an ortho- or meta-linkage structure.

The curable resin compound of the present invention has the following advantages.

While the curable resin compound exhibits satisfactory solubilities in organic solvents, a composition containing the compound can be cured by a crosslinking reaction which transform the composition into a cured-resin material which is insoluble in the organic solvents and is provided with improved solvent and chemical resistance, and in addition, improved thermal resistance. Further, such a cured-resin material exhibits excellent mechanical performance and strength.

Accordingly, by utilizing the soluble state in organic solvents, the curable resin compound of the present invention can be used for various matrix resins, coating materials, binders, or the like, and can be used in various molding methods for producing various molded products. In other words, the curable resin compound or the cured-resin material of the present invention is provided with remarkably broad applicability. Specifically, the curable resin compound can be applied to various molding methods in addition to compression molding and extrusion molding.

Further, the curable resin compound of the present invention has a low curing temperature, and therefore, can be easily handled. By curing and crosslinking a composition comprising the compound after molding, the resultant cured-resin material can exhibit markedly high solvent resistance, chemical resistance, and mechanical strength. The cured-resin material is, therefore, available as an excellent resin material.

Moreover, because of having no ester groups, the curable resin compound of the present invention has high moisture resistance and is rarely hydrolyzed; namely, the compound is excellent in stability.

Particularly, the curable resin compound recited in the above paragraph (1) is excellent especially in solubility because of its low molecular weight. Further, in the curable resin compound recited in the above paragraph (2), the degree of polymerization can be easily controlled; namely, the degree of crosslinking can be controlled.

Additionally, the molecular weights of the curable resin compound of the present invention can be controlled ad libitum by controlling the quantitative ratio between reactants, i.e. the relative amounts of dihydrobenzophenone and dibromobenzene to be introduced into the reaction for producing the compound. Accordingly, the thermal expansion coefficient of the compound can be adjusted in accordance with the objective final product.

DESCRIPTION OF THE PREFERRED EMBODIMENT

As is described above, the curable resin compound of the present invention is characterized in that a crosslinking reaction transforms a composition comprising the compound into a cured-resin material which is insoluble in organic solvents, though the compound itself is satisfactorily soluble in organic solvents.

The curable resin compound of the present invention recited in the above paragraph (1) has a structure in which a plurality of benzene rings are joined by ether and ketone linkages. Specifically, mutually adjacent benzene rings are joined by only an ether linkage or an ketone linkage, while the structure contains both types of the linkages. Further, the compound is characterized in that the number of benzene rings is 4 or less, and more specifically, as small as 3 or 4, and each benzene ring in the structure has no substituents. Moreover, the structure is end-capped with crosslinkable groups.

As described above, the curable resin compound comprises a low number of non-substituted benzene rings, and therefore, the curing temperature for crosslinking the compound can be decreased and the solubility in solvents can be improved. Further, the cured-resin materials derived from the curable resin compound are excellent in chemical and solvent resistances.

Concerning a known-art resin compound which originally has a high solubility and can be transformed into a cured-resin material, Inventors previously made a patent application (laid-open as Japanese Unexamined Patent Publication No. 8-73548) which discloses a soluble acetylene-terminated poly(ether-ketone), wherein the curing temperature of the poly(ether-ketone) is as high as 250° C.

In general, furnaces applicable at a temperature of about 230° C. or less have been used for curing phenol resins or epoxy resins, each of these resins being conventionally and generally used as a binder resin which is one application mode of the present invention, since these resins can be cured by heating to around 200° C.

Accordingly, some troubles or problems can be caused when furnaces conventionally and generally used for curing phenol resins or epoxy resins are used for curing the above poly(ether-ketone). For example, sufficient cure cannot be achieved due to a insufficient heating temperature. In such a case, the cured-resin material cannot exhibit the expected solvent resistance, or a longer curing time is required.

In contrast, the curable resin compound of the present invention can be cured at a low temperature of approximately 210° C. and therefore, can be sufficiently cured using furnaces conventionally and generally used. Accordingly, qualities and mass-productivities of objective products can be improved by using the curable resin compound of the present invention without any new plant and new equipment investment.

The examples of the curable resin compound according to the present invention recited in the above paragraph (1) may include the compounds expressed by chemical formulae i to viii below.

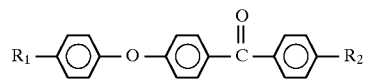

i

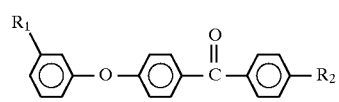

ii

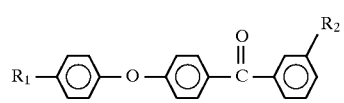

iii

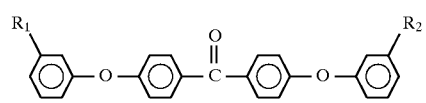

iv

-continued

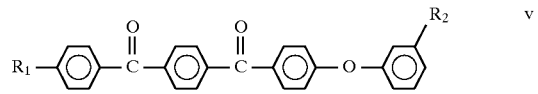

v

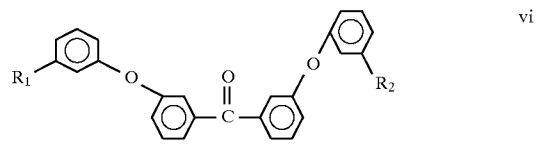

vi

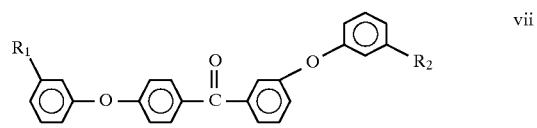

vii

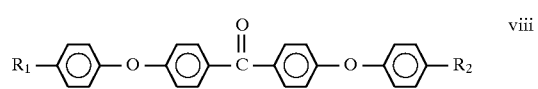

viii

In the above chemical formulae, the crosslinkable groups $R_1$ and $R_2$ may be groups of thermal crosslinking type, photo crosslinking type, ultraviolet crosslinking type, electron-ray crosslinking type, or the like. Examples of such a group are an ethynyl group, an allyl group, an epoxy group, and a vinyl group. Particularly, thermally crosslinkable groups are preferable, and more particularly, an ethynyl group is preferable since the cured material derived from the compound can be three-dimensional and provided with a high thermal resistance.

Further, the curable resin compound recited in the above paragraph (2) is a polymer, the repeating unit of which comprises a plurality of benzene rings joined with ether linkages and ketone linkages wherein at least one benzene ring in the repeating unit has an ortho- or meta-linkage structure. Also, the polymer is characterized in that the number of benzene rings in the repeating unit is as small as three or four, and that each benzene ring in the repeating unit has no substituents.

Examples of such a polymer comprising repeating units include the polymers expressed by the following chemical formulae I to IX.

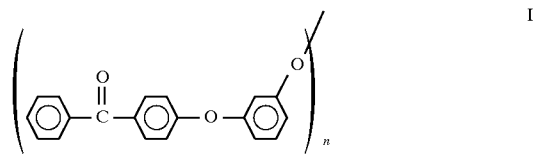

I

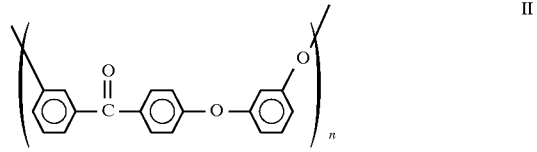

II

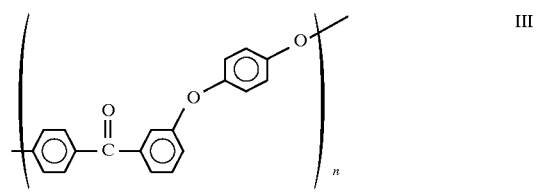

III

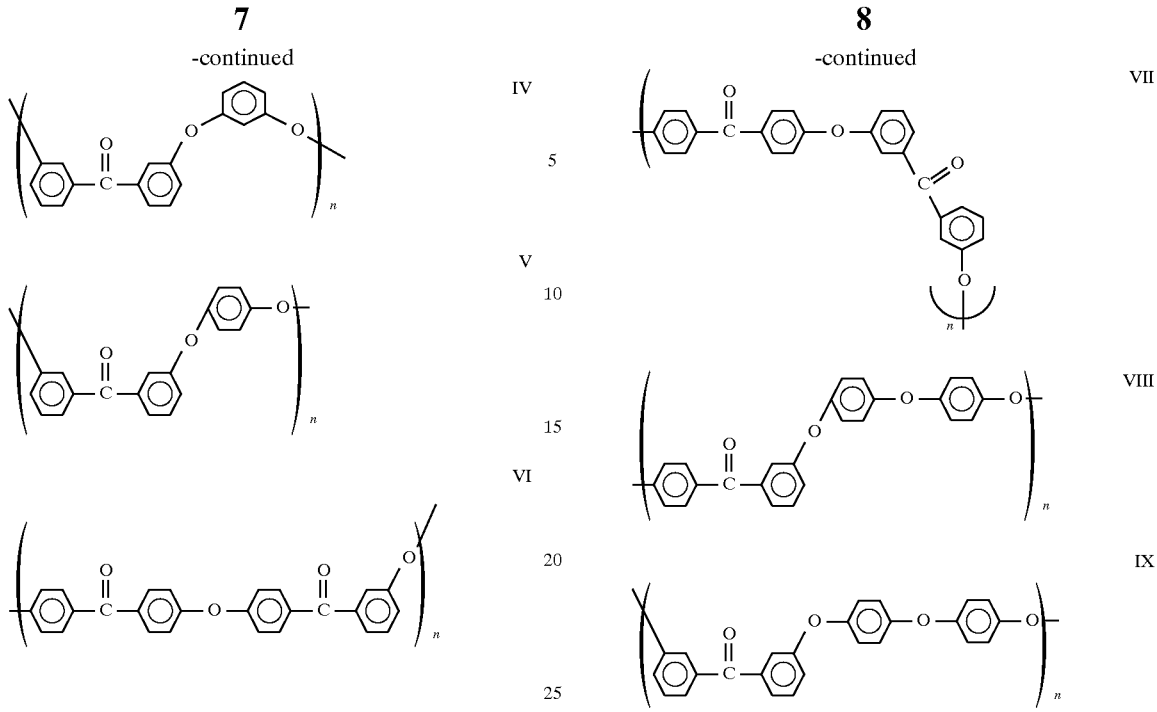

In a form of the curable resin compound recited in the above paragraph (2), each above polymer comprising repeating units is end-capped with crosslinkable groups $R_1$ and $R_2$, as expressed by the chemical formula below.

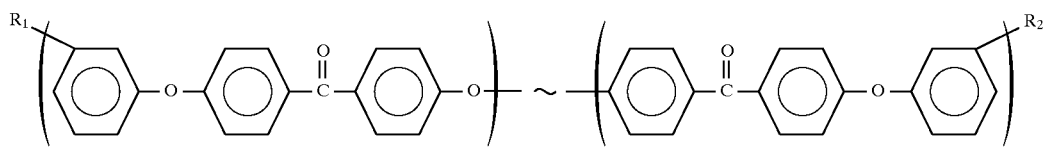

Here, decreasing the degree of polymerization n leads to increasing the relative number of end-capping crosslinkable groups in the cured resin material to be produced from the resin compound by a crosslinking reaction, and due to this, the cured resin material will have improved characteristics such as higher thermal resistance and higher mechanical strength.

As described above, in the curable resin compound of the present invention, the number of benzene ring in the base structure is small, each benzene ring has no substituents except for end-capping groups, and further, at least one benzene ring in the base structure has a linkage structure other than para-linkage structure. According to these features, the curable resin compound can possess a low crystallinity and improved solubility in solvents. Also, the temperature for curing the resin compound by crosslinking can be decreased, and in addition, the produced cured-resin material can possess a higher solvent resistance.

In other words, solubility of a curable resin compound can be improved by treatments for decreasing its crystallinity, and one example of such treatments is providing a meta-linkage structure for one or more benzene rings in the resin compound as shown in the following chemical formula. According to this treatment, the polymer itself becomes bent, and thereby, its crystallinity becomes low and the polymer becomes more soluble in ordinary solvents. Additionally, providing an ortho-linkage structure for one or more benzene rings also makes the polymer bent, and causes a similar effect as providing a meta-linkage structure (a non-para-linkage structure).

The curable resin compound recited in the above paragraph (1) can be produced, for example, by subjecting an aromatic ether-ketone end-capped with Br, I, or Cl to a reaction with an ethynyl-substituted tertiary alcohol or a silylacetylene in the presence of a palladium catalyst, the aromatic ether-ketone comprising three or four non-substituted benzene rings each of which joined with each adjacent benzene ring by an ether linkage or ketone linkage so that both types of linkages are present in the aromatic ether-ketone.

The curable resin compound recited in the above paragraph (2) can be produced, for example, by subjecting a

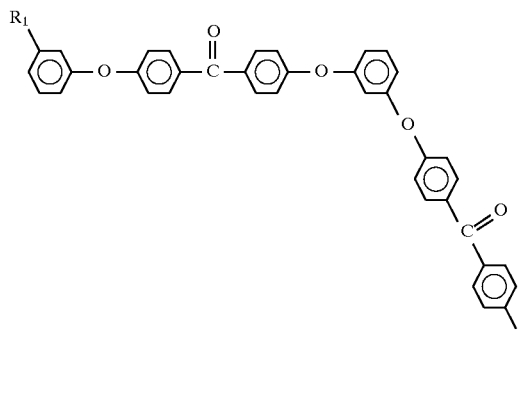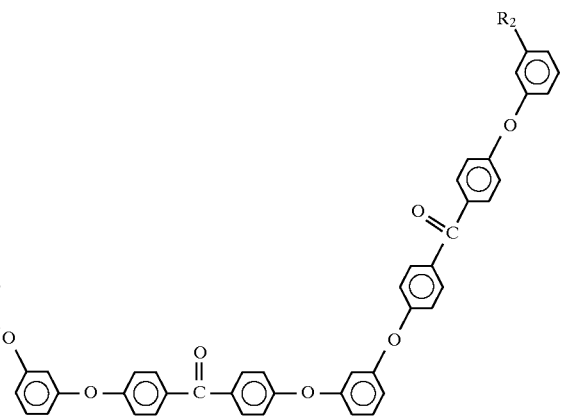

The curable resin compound of the present invention is highly soluble in various organic solvents which are generally used, for example, chloroform, tetrahydrofuran (THF), N,N'-dimethylformamide (DMF), N-methyl 2-pyrrolidone, and Triglyme.

A composition comprising the curable resin compound of the present invention can be transformed into a cured-resin material by a crosslinking reaction in the crosslinkable groups which end-cap the resin compound. The crosslinking reaction is achieved with thermal energy, photo energy, ultraviolet, electron rays, or the like.

The cured resin material obtained by a crosslinking reaction becomes insoluble in organic solvents, and is provided with improved solvent and chemical resistance. In addition, improved thermal resistance is also provided for such cured-resin materials in many cases.

Accordingly, by utilizing the soluble state in organic solvents, the curable resin compound of the present invention can be used for various matrix resins, and can be applied to various molding methods for producing various molded products. In other words, the curable resin compound or the cured-resin material of the present invention is provided with remarkably broad applicability.

In addition, by being crosslinked and cured after molding, the curable resin compound or the cured resin material will exhibit remarkably high solvent resistance, chemical resistance, and mechanical strength, and therefore, is available as an excellent resin material.

Particularly, the curable resin compound or the cured resin material is suitable for materials for electrical resistor members or for moistureproof coating materials. For example, it can be used as a binder resin for a carbon resistor member or as a moistureproof coating material for semiconductors. To be used for a resistor member of a variable resistor, for example, the curable resin compound is mixed with carbon to prepare a resistive paste, and subsequently baked.

polymer end-capped with Br, I, or Cl to a reaction with an ethynyl-substituted tertiary alcohol or a silylacetylene in the presence of a palladium catalyst, the polymer comprising repeating units comprising three or four non-substituted benzene rings each of which is joined with each adjacent benzene ring with an ether linkage or ketone linkage so that both types of linkages are present in the repeating unit and at least one benzene ring in the repeating unit has an ortho- or meta-linkage structure.

In the above production processes, 2-methyl-3-butyne-2-ol is used as a reactant for producing a curable resin compound which is end-capped with ethynyl groups as crosslinkable groups. Here, when allyl groups are used as end-capping crosslinkable groups, the corresponding allyl alcohol should be suitably used instead of 2-methyl-3-butyne-2-ol. Similarly, glycidol is suitable for end-capping with epoxy groups, and vinylphenol is suitable for end-capping with vinyl groups.

Additionally, the molecular weight of the curable resin compound of the present invention can be controlled ad libitum by controlling the quantitative ratio between reactants, i.e. the relative amounts of dihydrobenzophenone and dibromobenzene to be introduced into the reaction for producing the compound. Accordingly, the thermal expansion coefficient of the compound can be adjusted in accordance with the objective final product.

Example 1

As a curable resin compound of the present invention, 4,4'-bis(3-ethynylphenoxy)benzophenone was synthesized.

Synthesis of the Precursor 1

4,4'-Bis(3-bromophenoxy)benzophenone, which is the precursor of the objective compound, was synthesized first.

A reaction mixture was prepared with 3.8g (22 mmol) of m-bromophenol, 20 ml of methanol, and 20 ml of benzene.

To this reaction mixture, 20 ml of 1 N KOH was added while N₂ gas was passed into the mixture, and the methanol and water were removed at a temperature of 100° C. or below. To the resultant, 20 ml of benzene was added and benzene was distilled off at a temperature of 100° C. or below. Subsequently, 2.18 g (10 mmol) of 4,4'-difluorobenzophenone and 30 ml of dimethylsulfoxide (DMSO) was added and reacted at 140° C. for 4 hours to obtain 3.8 g of 4,4'-bis(3-bromophenoxy) benzophenone. The yield was approximately 72%. The following is the reaction formula of this synthesis.

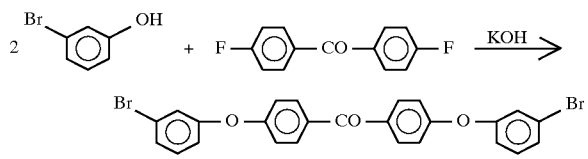

Synthesis of the Precursor 2

4,4'-Bis(3-bromophenoxy)benzophenone can be synthesized by the following process.

A reaction mixture was prepared with 3.8 g (22 mmol) of m-bromophenol, 2.18 g (10 mmol) of 4,4'-difluorobenzophenone, 10 ml of dimethylacetamide (DMAc), 15 ml of toluene and 4.55 g of K₂CO₃, and reacted at 130° C. for 1 hour while N₂ gas was passed into the mixture. Subsequently, the reaction temperature was raised to 160° C. to remove toluene and water in the reaction vessel as an azeotropic mixture, and the reaction was continued for 2 hours to obtain 5.25 g of 4,4'-bis(3-bromophenoxy) benzophenone. The yield was approximately 100%.

This process was found to bring about a markedly high yield.

Synthesis of 4,4'-Bis(3-ethynylphenoxy) benzohenone 4,4'-Bis(3-ethynylphenoxy)benzophenone was synthesized by using 4,4'-bis(3-bromophenoxy)benzophenone prepared above.

In 20 ml of triethylamine, dissolved are 1.4 g (2.7 mmol) of 4,4'-bis(3-bromophenoxy)benzophenone and 0.67 g (8 mmol) of 2-methyl-3-butyne-2-ol. Through this reaction mixture, N₂ gas was allowed to flow for 20 min. To the resultant, 0.02 g of triphenylphosphine, 0.005 g of a palladium catalyst, i.e. (Ph₃P)₂PdCl₂, and 0.005 g of copper iodide were added and reacted at 80° C. for 20 hours. The reaction mixture was then washed with water and subjected to extraction with methylenechloride. A intermediate reaction product was obtained by removal of the methylenechloride. To this intermediate reaction product, 20 ml of toluene, 10 ml of methanol, and 0.8 g of NaOH were added, and subsequently, the methanol and a portion of the toluene were distilled off at a temperature of 100° C. The resultant was then washed with water and subjected to extraction with methylenechloride. Finally, the extracting solvent was removed to obtain 1.3 g of 4,4'-bis(3-ethynylphenoxy) benzophenone. The yield was approximately 94%. The following is the reaction formula of this synthesis.

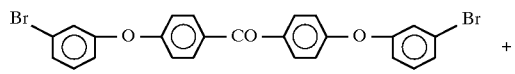

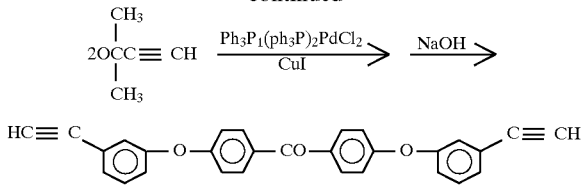

In the above synthesis procedure, 2-methyl-3-butyne-2-ol is used, which is one species of tertiary alcohol wherein one substituent is an acetylene group. Instead of such tertiary alcohols, silylacethylene such as trimethylsilylacetylene expressed by the chemical formula below may be used.

Also, the synthesis can be performed using 3-ethynylphenol expressed by the chemical formula below.

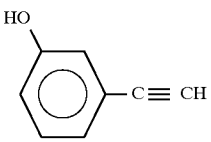

The use of 3-ethynylphenol, however, requires performing the reaction at 170° C. approximately, and is disadvantageous since 3-ethynylphenol itself is expensive.

In contrast, the use of the above-mentioned 2-methyl-3-butyne-2-ol enables the reaction to be performed at 80° C. approximately, and therefore, production of the objective compound is easier. In addition, 2-methyl-3-butyne-2-ol can be purchased at a low cost, for example, 0.1% of the cost for 3-ethynylphenol.

Furthermore, the use of 3-ethynylphenol causes the addition of benzene rings as well as the objective addition of ethynyl groups, and therefore, is not suitable to synthesis of a compound designed to have a small number of benzene rings. Meanwhile, the use of 2-methyl-3-butyne-2-ol can achieve the addition of ethynyl groups alone, and therefore, is advantageous to synthesis of a compound designed to have a small number of benzene rings.

Example 2

As a curable resin compound of the present invention, a set of acetylene-terminated poly(ether-ketones) was synthesized.

Synthesis of the Precursor

A set of bromine-terminated poly(ether-ketones), which is the precursor of the objective compound, was synthesized first.

Two point eight grams (13 mmol) of 4,4'-dihydroxybenzophenone was dissolved in 30 ml of DMAc, and 1.8 g of KOH in 2 ml of water was added. The mixture thus obtained was stirred at 90° C. for 15 min. while N₂ gas was passed into the mixture. Thirty ml of toluene was added and removed as an azeotropic mixture with water by heating to 150° C. To the resultant mixture, 0.4 g (3 mmol) of Cu₂O, and further, 4.1 g (16 mmol)of m-dibromobenzene were added, and the reaction was performed for 10 hours to obtain 3 g of a set of bromine-terminated poly(ether-ketones). The yield was approximately 64%. The following is the reaction formula of this synthesis.

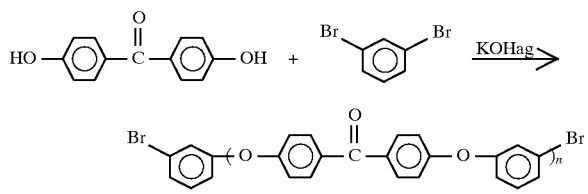

Synthesis of Acetylene-terminated Poly(ether-ketone)

A set of acetylene-terminated poly(ether-ketones) was synthesized by using the set of bromine-terminated poly(ether-ketones) prepared above.

In 20 ml of triethylamine, dissolved were 3 g (3 mmol) of the set of bromine-terminated poly(ether-ketones) (Mn: 1,000) and 0.75 g (8.9 mmol) of 2-methyl-3-butyne-2-ol. Through this reaction mixture, $N_2$ gas was allowed to flow for 20 min. To the resultant, 0.02 g of triphenylphosphine, 0.005 g of a palladium catalyst, i.e. $(Ph_3P)_2PdCl_2$, and 0.005 g of copper iodide were added and reacted at 80° C. for 24 hours. The reaction mixture was then washed with water and subjected to extraction with methylenechloride. A intermediate reaction product was obtained by removal of the methylenechloride. To this intermediate reaction product, 20 ml of toluene, 10 ml of methanol, and 0.8 g of NaOH were added, and subsequently, the methanol and a portion of the toluene were distilled off at a temperature of 100° C. The resultant was then washed with water and subjected to extraction with methylenechloride. Finally, the extracting solvent was removed to obtain 2.8 g of a set of acetylene-terminated poly(ether-ketones). The yield was approximately 93%. The following is the reaction formula of this synthesis.

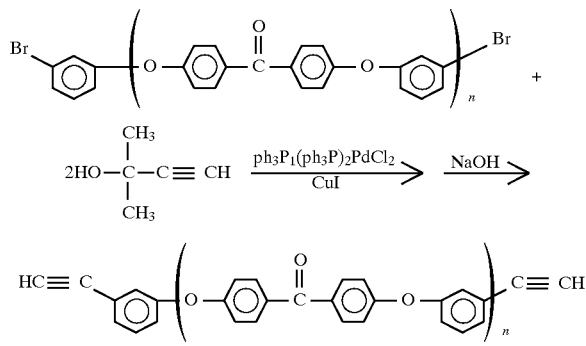

Solubility Test

Solubilities in various solvents were measured on the acetylene-terminated poly(ether-ketones) of various molecular weight values.

The molecular weight values were determined by gel permeation chromatography using an RI-8012 apparatus (manufactured by Tosoh Corporation), a column packed with gel having pore sizes of approximately 500,000 (manufactured by Hitachi Chemical Co., Ltd.), chloroform as a solvent, and polystyrenes as standard samples.

Solubilities were visually evaluated. Specifically, each 0.1 g of the acethylene-terminated poly(ether-ketones) was added to each 1 g of various solvents (DMAc, chloroform, methylene chloride, and methyl benzoate), and the cases in which the solute seemed to be completely dissolved were graded as "soluble". Similarly, the cases in which a slight amount of insoluble residue appeared were graded as "slight insoluble residue", and the cases in which insoluble residue apprently appeared were graded as "insoluble residue". The results are shown in Table 1 below.

TABLE 1

| No. | Molecular Weight | DMAc | Chloroform | Methylene Chloride | Methyl Benzoate |
|---|---|---|---|---|---|
| 1 | 21,000 | Insoluble Residue | Soluble | Soluble | Insoluble Residue |
| 2 | 10,000 | Insoluble Residue | Soluble | Soluble | Insoluble Residue |
| 3 | 4,000 | Soluble | Soluble | Soluble | Slight Insoluble Residue |
| 4 | 2,800 | Soluble | Soluble | Soluble | Soluble |
| 5 | 1,000 | Soluble | Soluble | Soluble | Soluble |

As is obvious from the results shown in Table 1, the polymer can be soluble in any solvents if the molecular weight of the polymer is 2,800 or less.

Example 3

The curable resin compound of the present invention expressed by the above-described chemical formula i was synthesized.

In 40 ml of a 10:1 mixture of methanesulfonic acid and diphosphorus pentoxide, 2.49 g of 4-bromodiphenyl ether and 2 g of 4-bromobenzoic acid are dissolved and reacted at 80° C. for 5 hours. After the reaction was completed, the reaction mixture was added into 1 liter of water and neutralized with sodium carbonate, and a reaction product was separated by filtration. The reaction product was then washed with water several times and vacuum-dried to obtain 4.15 g of a precursor.

Two point five grams of the precursor thus synthesized was dissolved in a mixture of 50 ml of pyridine and 15 ml of triethylamine, and further, 2.52 g of 2-methyl-3-butyne-2-ol was added and stirred. To this mixture, 0.083 g of triphenylphosphine, 0.021 g of copper iodide, and 0.021 g of a palladium catalyst, i.e. $(Ph_3P)2PdCl_2$, were added under $N_2$ gas stream, and reacted at 85° C. for 24 hours. The reaction mixture was then cooled and filtrated, and the solvent was removed from the filtrate followed by the addition of chloroform. After being washed with a 10% sulfuric acid solution and washed with water several times, the resultant was subjected to removal of chloroform to obtain a reaction product. Subsequently, 50 ml of toluene and 20 ml of methanol were added to the reaction product. Further, 1.66 g of NaOH was added and the resultant mixture was heated to 90 to 100° C in order to distill off the methanol and a portion of the toluene. The reaction mixture thus obtained was then cooled and was washed by adding sodium bicarbonate, and the resultant organic layer was taken out and washed with water several times. When the organic layer was not sufficiently separated from the aqueous layer, chloroform was added to the mixture and the resultant organic layer was taken out. Finally, sodium sulfate was added for drying, and the resultant was subjected to removal of the solvent to obtain 2.1 g of a brown and solid resin compound expressed by the above-described chemical formula i.

Example 4

The curable resin compound of the present invention expressed by the above-described chemical formula iii was synthesized.

Four point three grams of a precursor was prepared in the same manner as Example 3 above except that 3-bromobenzoic acid was used instead of 4-bromobenzoic acid.

By using 2.5 g of the precursor thus obtained, 3.4 g of a solid resin compound expressed by the above-described chemical formula iii was synthesized in the same manner as Example 3 above.

Example 5

The curable resin compound of the present invention expressed by the above-described chemical formula viii, i.e. 4,4'-bis(4-ethynylphenoxy)benzophenone was synthesized.

Five point two five grams of a precursor, i.e. 4,4'-bis(4-bromophenoxy)benzophenone was prepared in the same manner as "Synthesis of the Precursor 1" in Example 1 above except that p-bromophenol was used instead of m-bromophenol.

By using the precursor thus obtained, 0.91 g of 4,4'-bis(4-ethynylphenoxy)benzophenone was synthesized in the same manner as Example 1 above. The yield was approximately 66%.

Comparative Example 1

A resin compound having 5 benzene rings in its structure was synthesized as a comparative example.

At first, 2.18 g of 4,4'-difluorobenzophenone and 1.12 g of 4-fluorophenol were dissolved in a mixture of 20 ml of DMAc and 40 ml of toluene. To this mixture, 2.76 g of $K_2CO_3$ was added, and the resultant mixture was refluxed at 130° C. for 1 hour while $N_2$ gas was passed into the mixture. After that, the temperature was raised to 170° C. to distill off the toluene in the reaction vessel and to react the remaining mixture for 2 hours. Subsequently, the reaction mixture was transferred into 1 liter of water, and subjected to several times of filtration and washing, and dried to obtain 2.8 g of a slightly brownish powder. This powder was then dissolved in chloroform and purified using silica gel to obtain a precursor.

In a mixture of 10 ml of DMAc and 15 ml of toluene, 1.5 g of the above-prepared precursor, 1.25 g of 3-ethynylphenol and 2.6 g of potassium carbonate was dissolved, and the resultant mixture was refluxed at 130° C. for 1 hour under $N_2$ gas stream. The temperature was then raised to 165° C. to distill off the toluene and to react the remaining mixture for 2 hours. After the reaction was completed, the reaction mixture was transferred into 1 liter of water, and subjected to filtration and drying to obtain 2.2 g of a slightly-brownish solid resin compound.

Measurement of Exothermic Peak Temperature, Solubility Test and Solvent Resistance Test Measurement of Exothermic Peak Temperature Exothermic peak temperature was measured on each of the curable resin compounds expressed by the above-described chemical formulae i (Example 3), iii (Example 4), iv, and viii (Example 5); and the resin compound of Comparative Example 1.

Each measurement was performed using a differential scanning calorimeter (DSC 220, manufactured by Seiko Instruments Inc.) with an ascending temperature rate of 10° C./min under a nitrogen atmosphere.

The results are shown in Table 2 below.

Solubility Test '

On the same curable resin compounds as above, solubilities in DMAc were evaluated in the same manner as the solubility test in Example 2.

The results are shown in Table 2 below.

Solvent Resistance Test

The above curable resin compounds were cured, and the obtained cured-resin materials were subjected to a solvent resistance test.

At first, each curable resin compound was made into a varnish, and carbon black (Ketjen Black, manufactured by Ketjen Black International Company) was mixed at a ratio of about 3% by volume relative to the resin in the varnish. Using the ink thus prepared, a coating of an undefined shape was formed on a ceramic substrate. Subsequently, the resin compound in the coating was crosslinked and cured by heating at 210° C. for 15 min. The sample thus obtained was examined for its electrical resistance value under ordinary temperature and humidity.

Secondly, one portion of the sample was dipped in toluene, and the other portion was dipped in isopropanol. After being dipped for 24 hours, each portion was wiped to remove the solvent, and examined for its electrical resistance value. The rate of change in its electrical resistance value between before and after dipping was defined as the solvent resistance value. According to this definition, the sample which exhibits a small change in its electrical resistance value between before and after dipping in a solvent, namely, the sample which exhibits a small rate of change, is recognized as excellent in solvent resistance.

The results are shown in Table 2 below. Here, each value shown in the table is the larger one among the values of the portion dipped in toluene and the portion dipped in isopropanol.

TABLE 2

| Sample ID | Number of Benzene Ring | Exothermic Peak Temperature(°C.) | Solubility | Solvent Resistance Value (%) |
|---|---|---|---|---|
| i | 3 | 223 | Soluble | 0.7 |
| iii | 3 | 221 | Soluble | 0.5 |
| iv | 4 | 245 | Soluble | 1.6 |
| viii | 4 | 247 | Soluble | 1.8 |
| Comparative Example 1 | 5 | 273 | Slight Insoluble Residue | 15.7 |

As is obvious from the results shown in Table 2, the curable resin compounds of the present invention expressed by the above-described chemical formulae i, iii, iv and viii, respectively, have lower exothermic peak temperatures, namely, have low curing temperatures, as compared with the resin compound of Comparative Example 1. Additionally, these curable resin compounds of the present invention are satisfactory in solubility.

Further, the cured-resin materials derived from these curable resin compounds of the present invention are excellent in solvent resistance.

Consequently, resin compounds having four or less benzene rings in their structure have been found to have excellent properties. This event is considered to hold good for the polymers comprising repeating units which have four or less benzene rings in their structure.

Comparative Example 2

There was synthesized a set of polymers comprising repeating units in which the constituting benzene rings have no ortho- or meta-linkage structures.

At first, 1.379 g of 4,4'-difluorobenzophenone, 0.566 g of hydroquinone, and 1.74 g of potassium carbonate were dissolved in a mixture of 15 ml of DMAc and 20 ml of toluene. The resultant mixture was then refluxed at 130'C. for 1 hour while $N_2$ gas was passed into the mixture. After that, the temperature was raised to 170° C. to distill off the toluene in the reaction vessel and to react the mixture for 2 hours. Subsequently, the reaction mixture was transferred into 1 liter of water, and subjected to filtration and washing with water several times, and then dried to obtain 2.2 g of a set of polymers as a slightly-brownish powder. The theoretical molecular weight of the set of polymers was 3,000.

On the set of polymers thus obtained, solubilities in DMAc and chloroform were examined in the same manner as described above. As a result, insoluble residue was recognized in both solvents.

Further, the molecular weight distribution of the set of polymers was examined by gel permeation chromatography as follows: The set of polymers were dissolved in chloroform, and filtrated with a filter having a pore size of 1 μm; and the filtrate was subjected to chromatography. As a result, the set of polymers was found to have a wide molecular weight distribution and to comprise polymers having molecular weights of several hundreds. Consequently, the polymer comprising repeating units in which the constituting benzene rings has no ortho- or para-linkage structures was found to become insoluble in generally-used organic solvents when the molecular weight of the polymer is 1,000 or more.

What is claimed is:

1. A curable resin compound comprising a structure and crosslinkable groups which end-cap the structure, wherein the crosslinkable groups comprise ethynl, and wherein the structure consists of three non-substituted benzene rings each of which is joined with each adjacent benzene ring by an ether linkage and a ketone linkage so that both types of linkages are present in the structure.

2. The curable resin compound of claim 1, wherein at least one of the crosslinkable groups is joined with one of the substituted benzene rings at a meta position.

3. The curable resin compound of claim 1, wherein at least one of the crosslinkable groups is joined with one of the non-substituted benzene rings at an ortho position.

* * * * *

UNITED STATES PATENT AND TRADEMARK OFFICE
CERTIFICATE OF CORRECTION

PATENT NO.   : 5,864,050
DATED        : January 26, 1999
INVENTOR(S)  : Yoshihiro Taguchi et al.

It is certified that error appears in the above-identified patent and that said Letters Patent is hereby corrected as shown below:

On the title page,:

In the second column, line 4, replace "Resms" with --Resins--; and "Adhesm" with --Adhesion--.

Signed and Sealed this

Twentieth Day of July, 1999

Attest:

Q. TODD DICKINSON

*Attesting Officer*   Acting Commissioner of Patents and Trademarks